(12) United States Patent
Alberto et al.

(10) Patent No.: US 7,582,295 B2
(45) Date of Patent: *Sep. 1, 2009

(54) COMBINATION OF INTERCALATING ORGANOMETALLIC COMPLEXES AND TUMOR SEEKING BIOMOLECULES FOR DNA CLEAVAGE AND RADIOTHERAPY

(75) Inventors: Roger Ariel Alberto, Winterthur (CH); Pascal Jean-Marie Hafliger, Zurich (CH)

(73) Assignee: University of Zurich, Zurich (CH)

( * ) Notice: Subject to any disclaimer, the term of this patent is extended or adjusted under 35 U.S.C. 154(b) by 404 days.

This patent is subject to a terminal disclaimer.

(21) Appl. No.: 10/707,994

(22) Filed: Jan. 30, 2004

(65) Prior Publication Data
US 2005/0019254 A1 Jan. 27, 2005

Related U.S. Application Data (63) Continuation of application No. 09/913,788, filed as application No. PCT/EP00/01553 on Feb. 24, 2000, now Pat. No. 6,844,425.

(60) Provisional application No. 60/121,340, filed on Feb. 24, 1999.

(30) Foreign Application Priority Data
Mar. 12, 1999 (EP) .................................. 99200754

(51) Int. Cl.
*A61K 39/395* (2006.01)
(52) U.S. Cl. .............. 424/130.1; 424/179.1; 424/181.1; 424/182.1; 424/391.1
(58) Field of Classification Search .............. 424/179.1, 424/181.1, 182.1, 391.1, 391.3, 391.5, 391.9; 530/391.1, 391.3, 391.5, 391.9
See application file for complete search history.

(56) References Cited

U.S. PATENT DOCUMENTS 5,759,514 A * 6/1998 Mattes ...................... 424/1.65
5,776,894 A * 7/1998 Albert et al. ................... 514/11

FOREIGN PATENT DOCUMENTS

WO WO 93/21957 A1 * 11/1993
WO WO 93/21975 11/1993

OTHER PUBLICATIONS

Tommasi et al. (Inorg. Chem. 1995; 34: 1514-1523.*
Holley et al. (Cancer Research 1992; 52: 4190-4195).*
Fawwaz et al., *The Use of a Porphyrin Bifunctional Chelator for Labeling of a Monocolonal Antibody with Radioactive Manganese*, Journal of Nuclear Medicine, Proceedings of the 36th Annual Meeting, May 1989, p. 935-936, vol. 30, Published by the Society of Nuclear Medicine, United States of America.
Mercer-Smith et al., *The Biodistribution of Radiocopper-Labeled Compounds*; Advances in Experimental Medicine and Biology, 1989, p. 103, vol. 258, Published by Kluwer Academic Publishers Group, United States of America, pp. 103-121.
Lerman, L. S., Structural Considerations in the Interaction of DNA and Acridines, J. Mol. Biol. (1961) vol. 3, pp. 18-30.
Long, Eric C. et al., Commentary, On Demonstrating DNA Intercalation, Accounts of Chemical Research, Sep. 1990, vol. 23, No. 9, pp. 271-273.

* cited by examiner

*Primary Examiner*—Brandon J Fetterolf (57) ABSTRACT

The invention relates to molecules for treatment and diagnosis of tumors and malignancies, comprising a tumor seeking biomolecule, which is coupled to an intercalating moiety, which is capable of complexing a metal, which metal is preferably a radioactive metal, to the use of these molecules and to therapeutic and diagnostic compositions containing them.

33 Claims, 7 Drawing Sheets

FIG. 8

COMBINATION OF INTERCALATING ORGANOMETALLIC COMPLEXES AND TUMOR SEEKING BIOMOLECULES FOR DNA CLEAVAGE AND RADIOTHERAPY

APPLICATION CROSS REFERENCE

This application is a continuation of prior U.S. patent application Ser. No. 09/913,788 filed on Aug. 15, 2001, now U.S. Pat. No. 6,844,425 which is a national phase application under 35 U.S.C. Section 371 of International Application No. PCT/EP00/01553 filed Feb. 24, 2000, which claims benefit of U.S. Provisional Patent Application No. 60/121,340 filed Feb. 24, 1999 and European Patent Application No. 99200754.2 filed Mar. 12, 1999.

BACKGROUND OF INVENTION

The present invention relates to new molecules for the treatment and diagnosis of tumors. The invention furthermore relates to therapeutical compositions comprising one or more of these molecules and to the use of both in treatment and diagnosis of cancer.

The diagnosis and therapy of cancer still requires a large input from the pharmaceutical and chemical industry. Although a substantial effort is made to develop new treatments, there are still many tumor types for which no treatment exists. An additional problem is the formation of micrometastases, which cannot be diagnosed or treated.

An important problem in treatment is the similarity between normal cells and cancer cells. Treatments interfering with the growth of tumor cells will also interfere in the growth of healthy cells. Radiotherapy as it is now known consists essentially of an arbitrary cross-fire from outside the cell or the cytoplasm. Because this is a rather rough treatment surrounding cells and tissues might also be damaged leading to more or less severe side effects.

The provision of an improved radiotherapy and diagnostic method for cancer which uses very low amounts of radionuclides and leads to a direct treatment in the malignant cell is therefore highly desirable.

It is known that the metabolism of cancer cells differs from that of normal cells. In addition, cancer cells appear to have an increased membrane permeability in comparison to normal cells due to an increased expression of membrane receptors. The result is that the cancer cells are more permeable for biological vectors, like proteins and peptides.

The enhanced uptake of such biological vectors can be used in the diagnosis of tumors by binding a radionuclide to a protein, for example by iodination of tyrosine functions in the protein or by covalent coupling of radioactive metal complexes. These molecules combine a tumor seeking function and a radioactive function. Although these types of molecules have been used for diagnosis, their use in therapy was not yet described.

SUMMARY OF INVENTION

It is the object of the present invention to further improve on the above described molecules to come to an even better tailored treatment of malignant cells.

This object is achieved by the invention by the provision of a molecule in which three functions are combined. This molecule comprises a tumor seeking molecule, which is coupled to an intercalating moiety, which is capable of complexing a metal, which metal is preferably a radioactive metal. The molecule can be targeted specifically to the tumor by the tumor seeking molecule and be internalized by the cell. The intercalating moiety will then insert into the DNA strand and induce breaks. In addition, the radioactive metal will also lead to strand breaking of the DNA. The advantage of the new molecules is that they are specifically directed to the malignant cell and are taken up by the cell.

The tumor seeking molecule is preferably a biomolecule, such as a peptide or protein that is actively targeted to the tumor cell. Examples of these biomolecules are somatostatin-, neurotensin-, bombesin-receptor binding molecules, monoclonal antibodies, Penetratin™ peptides, and glycoproteins, and molecules binding to the GPIIb/IIIa receptors. The invention is however not limited to these examples and is more generally applicable to other tumor seeking agents as well. This category encompasses in addition compounds which are known to be transported into the nucleus or the nucleus membrane. Examples of these are anti-sense oligonucleotides, proliferating agents, like deoxy-uridine, and small molecules, like spermidine. The intercalating moiety is preferably an aromatic molecule with an intercalative binding affinity for double-stranded DNA. Examples of such aromatic compounds are compounds containing i.e. acridine, porphyrin, ellipticine, phenantroline, carbazole, benzimidazole or compounds with known cytostatic activity (antibiotics) from the class of tetracyclines (anthracyclines), such as daunorubicine, epirubicine or mixoxantrone and are functionalized with ligands able to coordinate the $[M(CO)_3]^+$ moiety. Examples of such ligands are those mentioned in EP-879 606 and additionally polyamino-polycarboxylates, phosphates and phosphonates, aliphatic or aromatic or mixed triamines and thiones.

The intercalating and tumor seeking functions are sometimes combined in existing molecules. Examples of intercalating agents combining an intercalating moiety and a peptide are actinomycin and triostin.

The radioactive molecule can be any radioisotope. Pure γ-emitting nuclides are preferred since their accompanying low range conversion electrons will lead to cleavage of bonds, which are close to the decaying nucleus. The dose burden to the patient remains thus very low.

Figure 1:
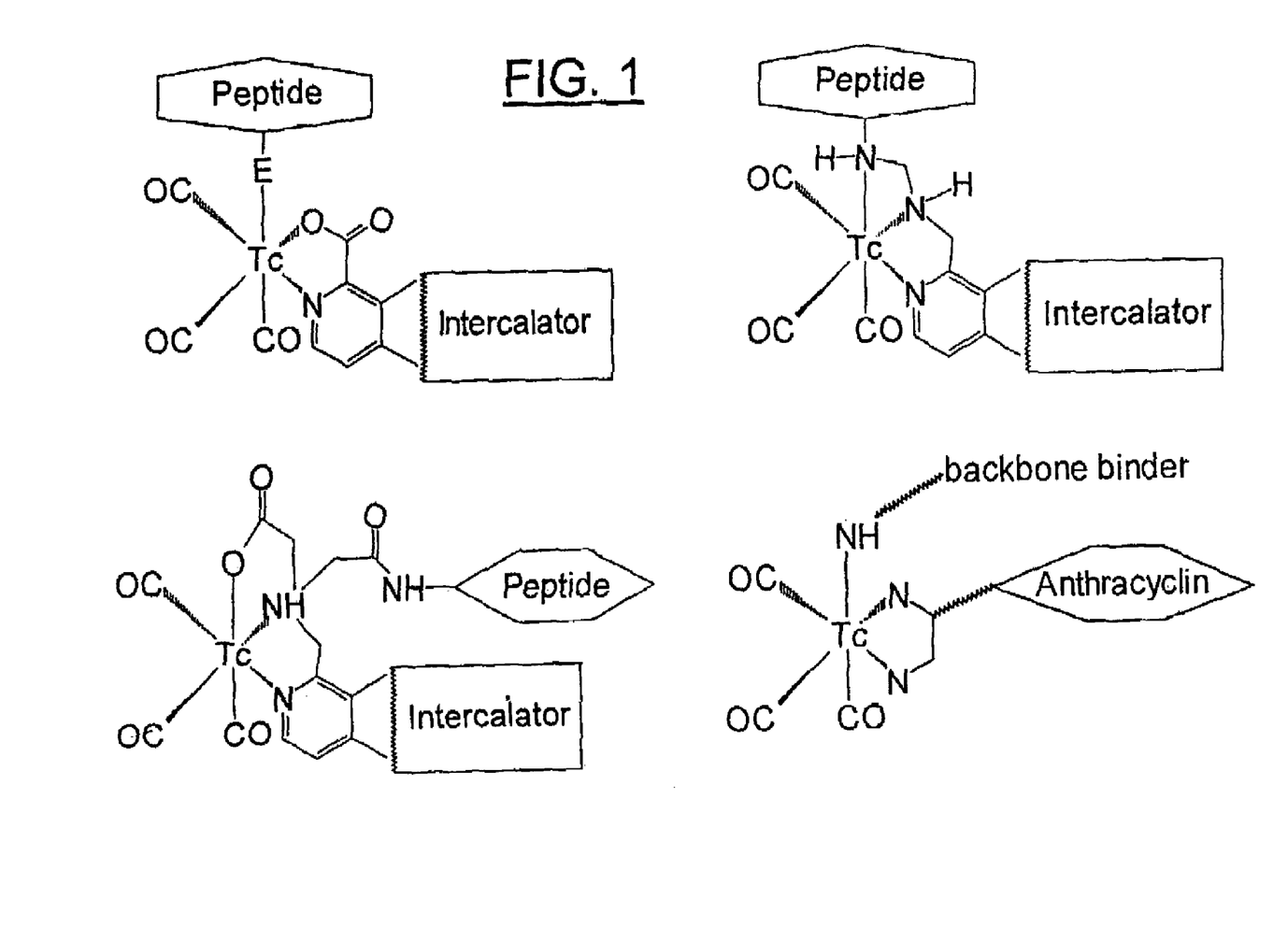
FIG. 1: schematic representation of potential molecules of the invention.

Particularly suitable combinations of the three functions are given in FIG. 1.

The invention further relates to the use of the molecules in therapy and diagnosis and to therapeutical and diagnostic compositions comprising one or more of these molecules.

Therapeutical compositions comprise at least a suitable amount of the molecule in a diluent or excipient. Such compositions can take the form of solutions and are administered intravenously, intraperitoneally or intrathecally. Suitable amounts to be administered depend on the way of administration, the radionuclide used and the indication to be treated or diagnosed. Suitable amounts vary between $10^{-9}$ and $10^{-1}$ g per kg body weight.

Excipients and diluents for this type of medication are well known to the skilled person. However, the present molecules require certain conditions for stability. Preferably, the excipient or diluent should be of a hydrophilic and preferably organic nature.

For diagnostic purposes the composition consists of at least a suitable amount of the molecule in a diluent or excipient. Diagnostic methods to be used with the composition of the invention are scintigraphy or Magnetic Resonance Imaging (MRI).

It was now found that the method for the synthesis of Tc and Re carbonyls from water described in EP-879 606 is suitable for preparation of the molecules of the invention. It is in particular possible with this method to introduce intercalating ligands, which form very stable complexes (in vitro and in vivo) with the above mentioned carbonyls. EP-879 606 is incorporated herein by reference.

The ligands claimed in EP-879 606 and acridine, porphyrin, ellipticine phenantroline, carbazole, benzimidazole do stabilize the fac-$[Tc(CO)_3]^+$ moiety in serum and form complexes at very low concentrations. These ligands can be site specifically attached to the biomolecules and subsequently be labeled with i.e. Tc-99m. Since the radionuclide is very close to the intercalating ligand, its low energy electron will penetrate the DNA-strands very well and induce strandbreaking. When intercalating in one of the grooves, the probability to hit is very high since the nucleus is practically surrounded by DNA.

The biomolecules derivatized according to the invention exhibit high selectivity and are internalized. As known from pure organic intercalators, the complex is going to intercalate in DNA in particular when the cell is dividing. In contrast with other therapeutics, a high selectivity can be achieved with this combination.

If Re-188 is applied as the radionuclide, the damages will be much more severe than in the case of Tc-99m, but, consequently, the applied amount of radioactivity will be much lower than in case of "normal" radiotherapy. Thus, severe side effects such as bone marrow toxicity could be avoided.

The present invention will be further illustrated in the examples that follow and which are solely intended to clarify the invention, but are in no way intended to be limiting to the scope thereof.

BRIEF DESCRIPTION OF DRAWINGS

In the Examples reference is made to the following figures.

DETAILED DESCRIPTION

EXAMPLES

Example 1

Synthesis of the Molecules of the Invention

1. Introduction

To provide a strong intercalation, the intercalator should be preferably planar and aromatic heterocyclic. Furthermore, pendant groups in the intercalator must stably be coordinated to the radionuclide (i.e. $^{99m}Tc$). In this example, it is not coercive that the coordinating unit must be a multidentate ligand with high thermodynamic stability, since most complexes with Tc(I) show an extremely high kinetic stability. For these reasons and due to the already known principles of complexation of several mono- and bidentate ligands (especially picolinic acid) 5,6-benzochinolin-3-carboxylic acid was selected as intercalator.

Figure 2:
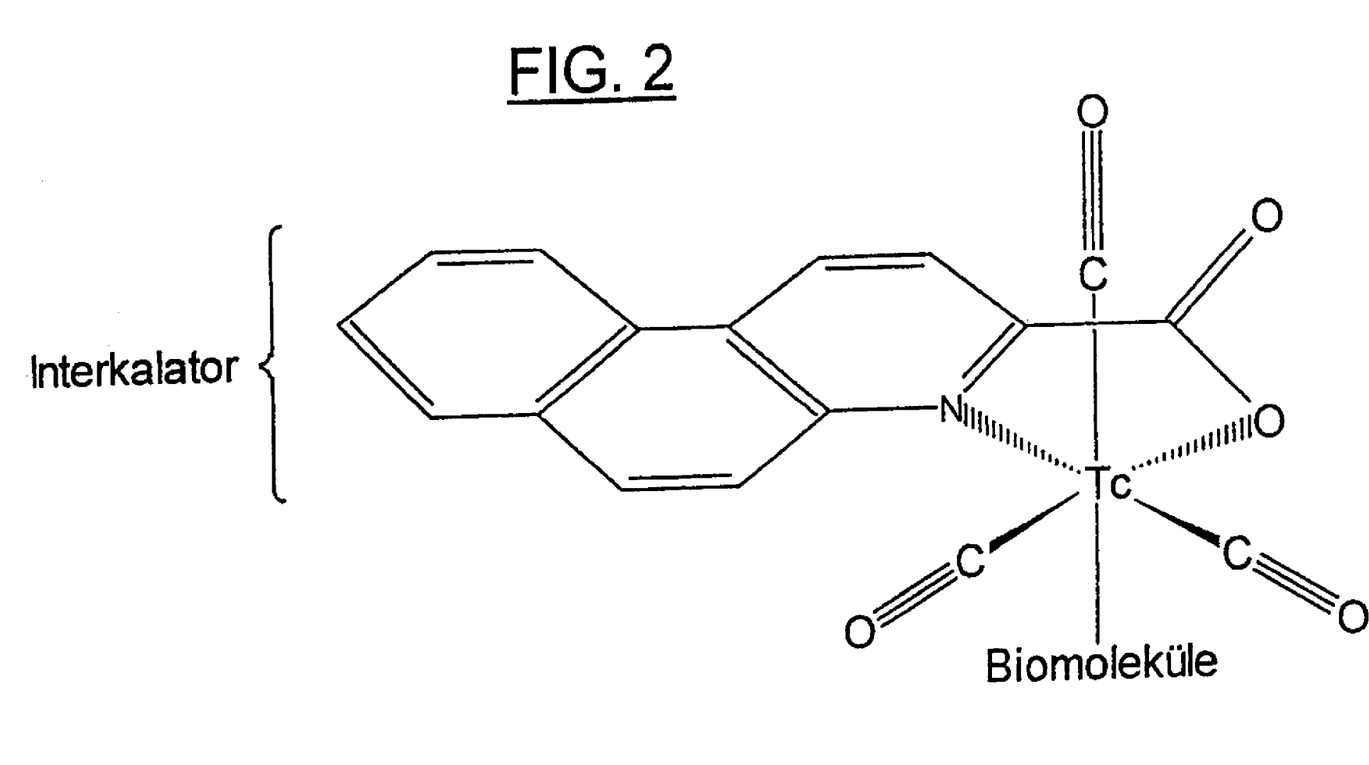
FIG. 2: example of a Tc(I) complex with this intercalating ligand and a potential biomolecule attached by direct linkage to another coordination site.

FIG. 2 depicts an example of a Tc(I) complex with this intercalating ligand and a potential biomolecule attached by direct linkage to another coordination site.

2. Synthesis of the Example Intercalator 2.1.
3-cyano-4-benzoyl-3,4-dihydrobenzo(f)chinoline 2

648 μl (5.58 mmol) benzoyl chloride was added to a two phase system of water/methylene chloride over a period of two hours. These two layers contain 500 mg (2.79 mmol) of benzo(f)chinolin in the methylene chloride layer and 545 mg (8.37 mmol) KCN in water. Stirring was continued for 6 hours. The organic phase was separated and washed with water, 5% hydrochloric acid, water, 5% NaOH solution, and again with water. After drying over magnesium sulfate, the solution was evaporated to dryness.

The bromide salt of this so-called Reissert-compound was recrystallized from 95% ethanol to yield the analytically pure substance. Yield: 612 mg (71%).

2.2 5,6-benzochinolin-3-carbon acid (P1)

2 ml 48% hydrobromide acid were added to 287 mg (0.93 mmol) of the Reissert-compound dissolved in 2 ml acetic acid. The solution was refluxed during 24 hours, cooled and filtered. The filtered product was washed with diethyl ether, dried, and recrystallized from methanol to yield 169 mg (0.76 mmol) (82%) of the hydrobromide of the intercalator as a yellow solid.

2.3 Macroscopic Synthesis of Technetium and Rhenium Complexes with P1
(5,6-benzochinolin-3-carbon acid)

2.3.1 [$NEt_4$][$ReBr(P1)(CO)_3$]
A suspension of 102 mg (133 μmol)
[$NEt_4$][$ReBr_3(CO)_3$], 29.7 mg (133 μmol) P1 and 116 μl (226 mmol) of trioctylamine were refluxed in dichloromethane until a clear solution was achieved. After evaporation of the solution, the complex 5 was extracted into THF. After evaporization of THF the residue was washed with diethyl ether to remove trioctyl ammonium bromide. Yield: 63 mg (67%) of the yellow complex.

2.3.2 [Re(P$_1$)(H$_2$O)(CO)$_3$]

200.0 mg (0.26 μmol) of [NEt$_4$]$_2$[ReBr$_3$(CO)$_3$] were refluxed in the presence of 29.1 mg of the intercalator P1 during 4 hours in 1M MES-buffer solution. Then the yellow precipitation was filtered. Yield: 114.2 mg (86%).

2.4 Microscopic Synthesis of [$^{99m}$Tc(H$_2$O)(P$_1$)(CO)$_3$]

The $^{99m}$Tc complexes were synthesized in a two-step procedure with a normal generator eluate. In a first step the complex was synthesized in >97% yield according to the literature (R. Alberto et al., J. Am. Chem. Soc. 120, 7987 (1998)). The solution was then neutralized with phosphate buffer in the reaction vial and a solution of the corresponding ligand was added. The end concentration was between 10$^{-4}$ and 10$^{-5}$. It was left standing for 30 minutes at 75° C. The radio-chemical purification and the yield were defined through HPLC-chromatography and it was discovered that [$^{99m}$Tc(HPO$_4$)(P1)(CO)$_3$]$^{2-}$ (compound 10) with a yield of 80-95% (dependent on the ligand concentration and the reaction time) was formed.

2.5 Synthesis of Model Trifunctional Molecules of the Invention

Figure 3:
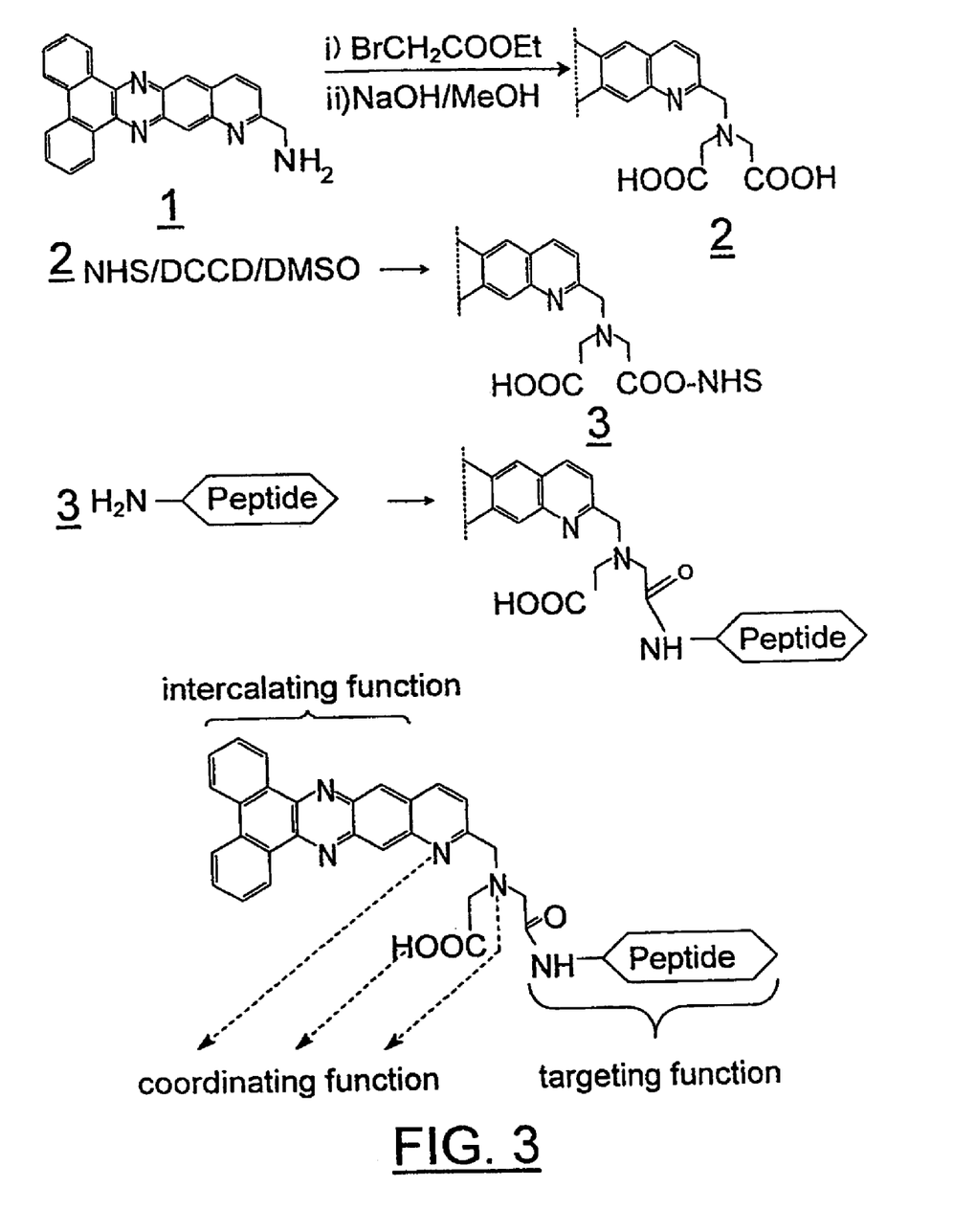
FIG. 3: schematic representation of the method for preparing molecules of the invention.

This is an example how a trifunctional molecule can be built. The procedure is based on known synthetic approaches for the corresponding coupling methods. The schematic procedure is given in FIG. 3.

1. Syntheses of the Bifunctional Ligands, Bearing an Intercalator and a Coordinating Functionality 2-Methylquinoline (1)

2-Methylquinoline (1) was bought from Fluka and used without further purification.

Quinoline-2-carbaldehyde (2)

A mixture of 5.5 g of selenium dioxyde (49.5 mmol) in 50 ml dioxane and 2 ml water was added in small portions over 10 minutes to a boiling solution of 4.4 g (30.7 mmol) of 2-methylquinoline (1) in 20 ml dioxane. After 6 hours of boiling, the warm reaction mixture was filtered. The filtrate was evaporated, dissolved in dichloromethane and filtered through Alox. The yellow-brown solid product obtained after evaporation of the solvent was recrystallized from dichlormethane. Yield: 3.76 g (78%).

$^1$H-NMR (DMSO): δ, 10.12s, 8.61d, 8.22d, 8.12d, 7.99d, 7.91t, 7.79t

Compound 3a

A mixture of 500 mg of quinoline-2-carbaldehyde (2) (3.2 mmol) and 330 mg of N-(2-aminoethyl)-acetamid (3.23 mmol) in 15 ml of methanol was stirred for 2 hours at room temperature. The light brown solid product obtained was directly used for the next reaction. Yield: ~770 mg (~100%).

$^1$H-NMR (CDCl$_3$): δ, 8.57s, 8.21d, 8.13d, 8.10d, 7.85d, 7.75t, 7.59t

Compound 3b

A solution of 175 mg (4.62 mmol) of NaBH$_4$ in 10 ml of ethanol was slowly added over 2 hours to a stirred solution of 500 mg (2.07 mmol) of 3a in 30 ml ethanol at 0° C. This mixture was then stirred overnight at room temperature. The solid substance obtained after evaporation of the solvent was triturated with a 3M Na$_2$CO$_3$ solution. The desired light brown product (3b) was then extracted with dichloromethane. Yield: 382 mg (76%).

$^1$H-NMR (CDCl$_3$): δ, 8.15d, 8.05d, 7.81d, 7.71t, 7.54t, 7.35d, 6.84br, 4.21s, 3.50q, 3.02t, 2.02s

Compound 3c

A solution of 200 mg of 3b (0.82 mmol) in 20 ml of 2N HCl was refluxed for 6 hours. The oil obtained after evaporation of the solvent was washed with ethanol to give the desired light brown solid hydrochloride salt 3c. Yield: 203 mg (90%).

$^1$H-NMR (D$_2$O): δ, 8.40d, 7.95t, 7.76t, 7.59t, 7.49d, 4.57s, 3.46t, 3.34t

N-BOC-diethylentriamine (4)

A solution of 500 mg (2.29 mmol) of di-tert-butyl dicarbonate ((BOC)$_2$O) in 30 ml dioxan was slowly added to a solution of 1.49 ml (1.42 g) (13.74 mmol) of diethylentriamine in 80 ml of dioxan at 10° C. The mixture was then stirred for 15 hours at room temperature. The desired product precipitated as an oil, which was then separated from the rest of the solution, dissolved in water, filtered, and extracted with dichloromethane to finally give the desired product as a light yellow oil. Yield: 260 mg (56%).

$^1$H-NMR (CDCl$_3$): δ, 5.15br, 3.25br, 3.18t, 2.77t, 2.69t, 2.63t, 1.76br, 1.41s, 1.19t

Compound 5a

A mixture of 140 mg of quinoline-2-carbaldehyde (2) (0.89 mmol) and 200 mg of N-BOC-diethylentriamine (0.99 mmol) in 30 ml of methanol was stirred for 3 hours at room temperature. The solid obtained after evaporation of the solvent was then washed with water to obtain the desired light brown product. Yield: 304 mg (94%).

$^1$H-NMR (DMSO): δ, 8.32d, 7.97t, 7.73t, 7.71d, 7.57t, 6.65t, 4.33s, 3.08t, 2.97t, 2.85t, 1.28s, 1.09t

Compound 5b

A solution of 41 mg (1.08 mmol) of NaBH$_4$ in 10 ml of ethanol was slowly added over 2 hours to a stirred solution of 148 mg (0.43 mmol) 5a in 30 ml of ethanol at 0° C. This mixture was then stirred overnight at room temperature. The solid brown oil obtained after evaporation of the solvent was triturated with a 3M Na$_2$CO$_3$ solution. The desired light brown product (3b) was then extracted with dichloromethane. Yield: 136 mg (92%).

$^1$H-NMR (DMSO): δ, 8.29d, 7.94d, 7.92d, 7.71t, 7.61d, 7.54t, 6.71t, 3.95s, 2.96q, 2.59s, 1.33s, 1.22t

Compound 5c

A solution of 100 mg of 5b (0.29 mmol) in 3N HCl was refluxed for 2 hours. The oil obtained after evaporation of the solvent was washed with diethylether to give the desired light brown solid hydrochloride salt 5c. Yield: 102 mg (94%).

$^1$H-NMR (D$_2$O):δ, 8.44d, 7.95t, 7.77t, 7.6t, 7.51d, 4.51s, 3.44s, 3.34t, 3.27t

2. Synthesis of Trifunctional Model Intercalators

Figure 8:
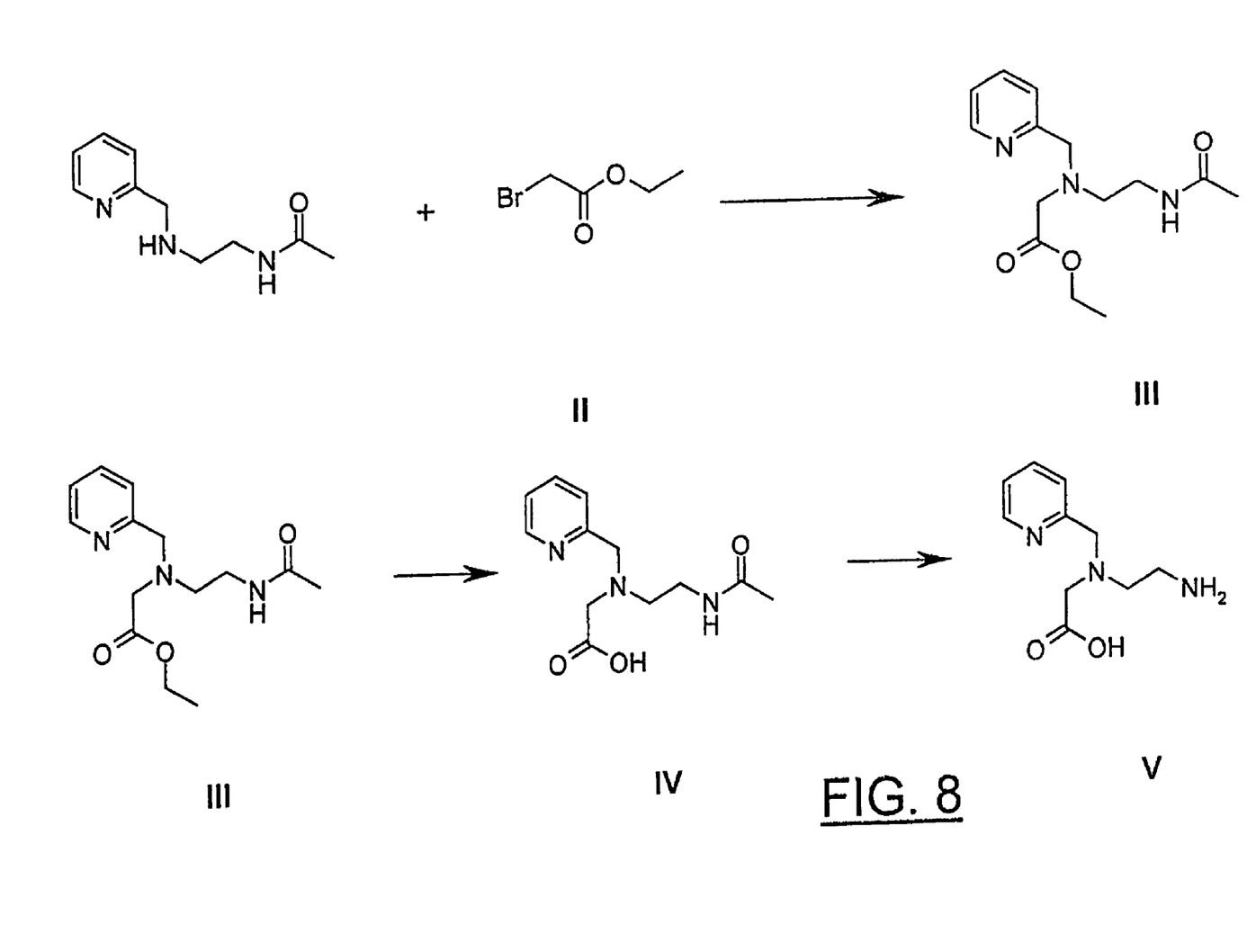
FIG. 8: reaction scheme for the preparation of model trifunctional intercalators.

Trifunctional intercalators were prepared starting from 5a or 3b of part 1 above. FIG. 8 gives the specific reaction scheme.

alkylation of an amine with bromo-aceticacid-ethylester

Figure 7:
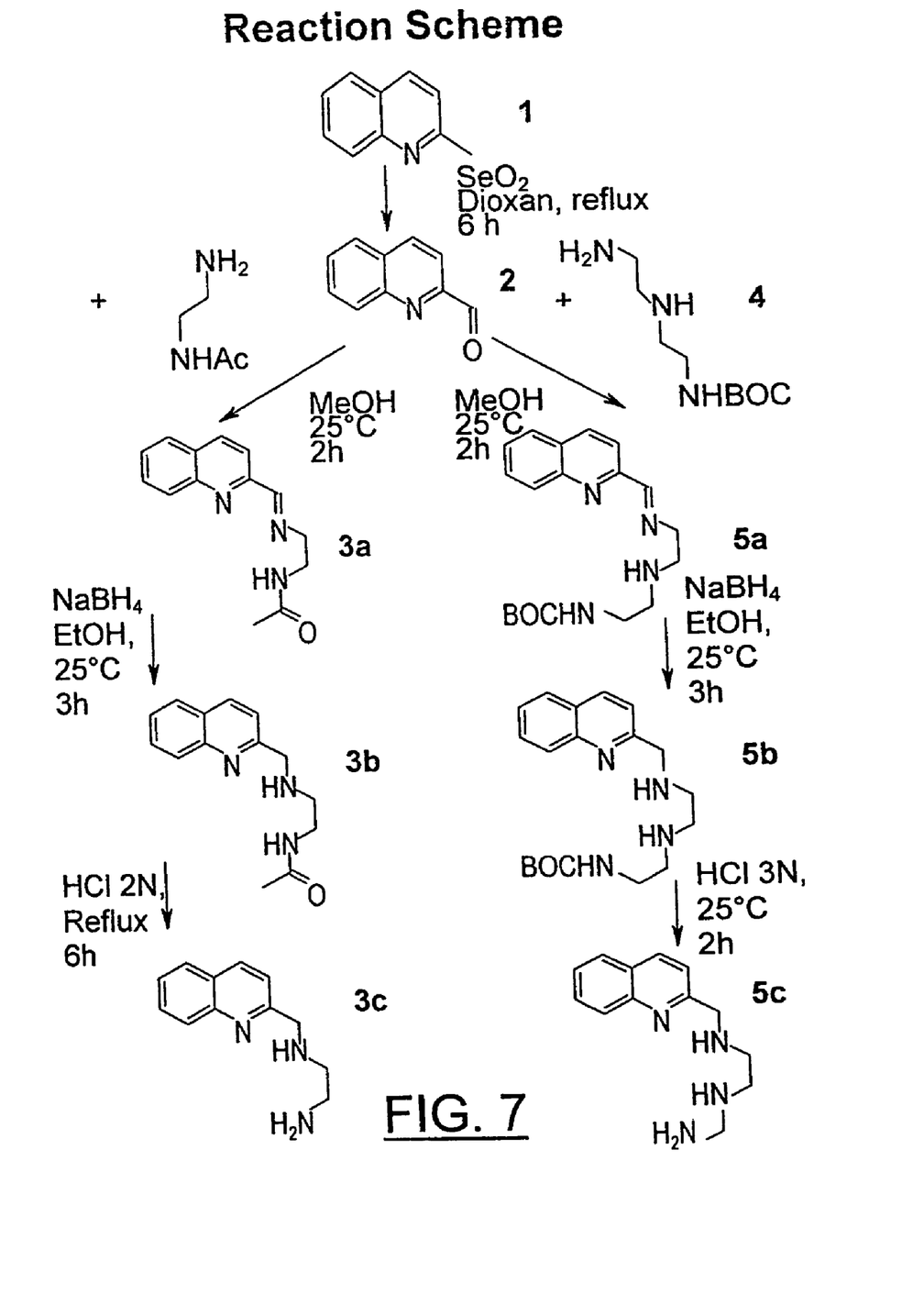
FIG. 7: reaction scheme for the preparation of model bifunctional intercalators.

Amine I (FIG. 7; 547 mg, 2.83 mmol) and triethylene amine (0.510 ml, 3.08 mmol) were stirred in methanol (10 ml). The solution was cooled to 0° C., and ethyl bromoacetate II (0.313 ml, 2.83 mmol) was added dropwise within 5 minutes. After stirring the solution at room temperature for 18 hours, the solvent was removed in vacuo. The residue was dissolved in dichloromethane (50 ml) and washed three times with water (20 ml). The water phases were washed twice with dichloromethane (50 ml). The organic phases were dried over $MgSO_4$, filtered, and the solvent was removed in vacuo to give III as a yellow oil. Yield: 590 mg (2.11 mmol, 74.6%).

TLC (silica, ethanol) $R_F$ 0.4

$^1$H NMR (200 MHz, $d_6$-acetone) δ=8.44 (m, 1H, picolin), 7.65 (m, 1H, picolin), 7.45 (m, 1H, picolin), 7.21 (m, 1H, picolin), 4.12 (q, 2H, J=7.2 Hz, $CH_2$ ester), 3.94 (s, 2H, $CH_2$), 3.64 (s, 2H, $CH_2$), 3.32 (m, 2H, N—$CH_2$—$CH_2$—N), 2.82 (m, 2H, N—$CH_2$—$CH_2$—N), 1.84 (s, 3H, $CH_3$—CO), 1.21 (t, 3H, J=7.2 Hz, $CH_3$ ester).

2. Deprotection

Amine III (576 mg, 1.94 mmol) was dissolved ethanol (4 ml) and water (8 ml). NaOH 2M (2 ml) was added, and the solution was stirred at room temperature for 1.5 hours. Analytical HPLC exhibited a single peak, indicating that the ester group was cleaved quantitatively.

The solvent was removed in vacuo, the residue was dissolved in water (8 ml), and HCl 2N (1 ml) was added to neutralize the solution. HCl 33% (1.0 ml) was added, and the reaction mixture was stirred at 90° C. for 48 hours. $NaHCO_3$ was added to neutralize the reaction mixture, the solvent was removed in vacuo and the residue was washed with ethanol. Removing of the solvent gave the deprotected product V as a yellow oil. Yield: 352 mmol (1.68 mmol, 68.6%).

$^1$H NMR (300 MHz, $D_2O$) δ=8.44 (m, 1H, picolin), 7.85 (m, 1H, picolin), 7.45 (m, 1H, picolin), 7.39 (m, 1H, picolin), 3.78 (s, 2H, $CH_2$), 3.35 (m, 2H, N—$CH_2$—$CH_2$—N), 3.22 (s, 2H, $CH_2$), 3.32), 2.79 (m, 2H, N—$CH_2$—$CH_2$—N).

Example 2

Strand Breaking with the Molecules of the Invention in a Model System

1. Introduction 1.1 The Use of Plasmids

To investigate the ability of the intercalating complexes with $^{99m}Tc$ to induce DNA-strandbreaks, plasmids were used as a model system. Plasmids are very suitable because electrophoretic analyses allow to differentiate between double and single strand breaks. Additionally, large quantities of plasmids can be produced very simply by using cell biological methods.

Figure 4:
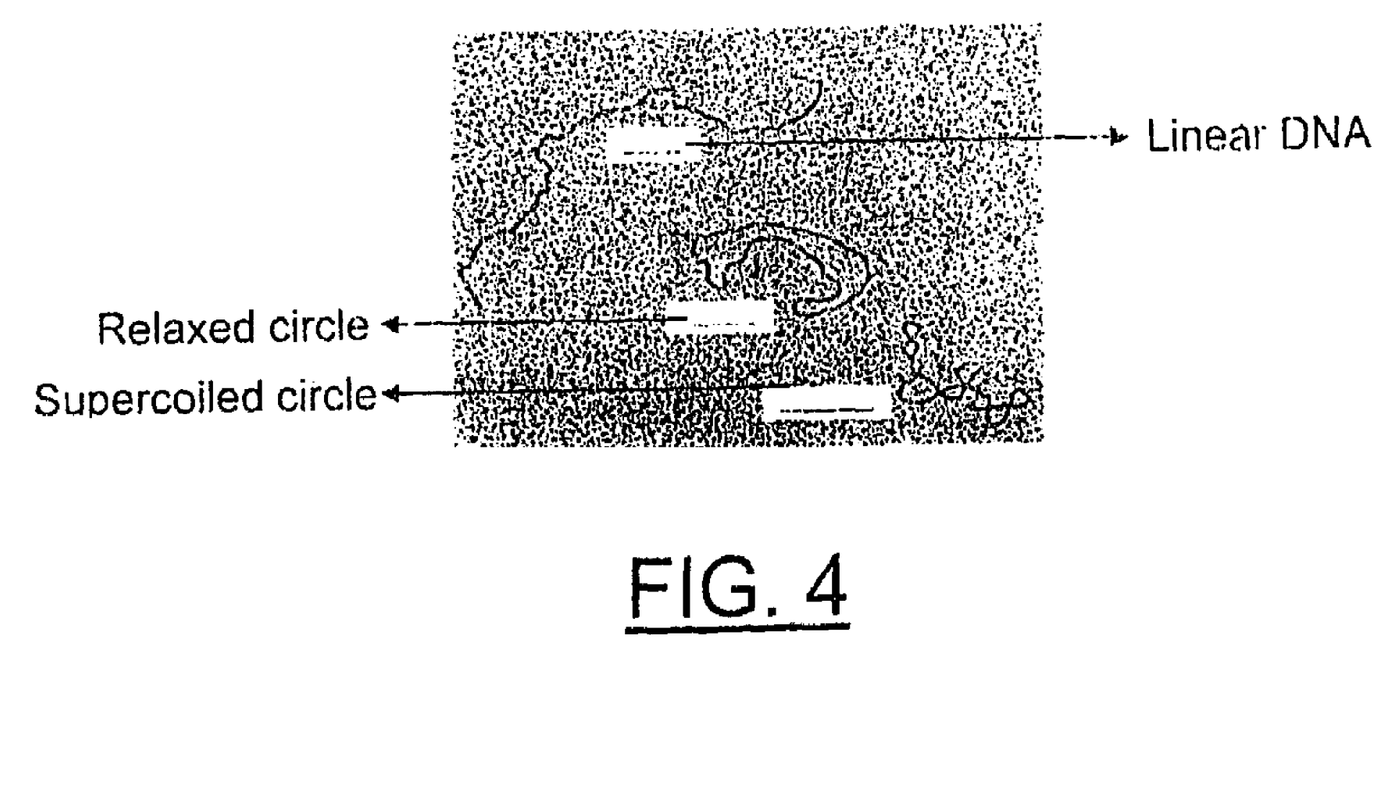
FIG. 4: schematic representation of the three types of plasmid structures.

A plasmid is a circular double-stranded DNA molecule, which double helical axis can be drilled into a superhelix. This form of the superhelix is described as type I. This type may loose its superhelix-structure by a single strandbreak and is then present as a relaxed circular DNA (type II). Through a double strandbreak of both types a linear from (type III) of the plasmid will be created. FIG. 4 shows an example of the structure of these 3 DNA types.

Because these three DNA types have different structures, they may well be separated due to their size and especially their form by electrophoresis on agarose gel. The mixture (type I-III after the experiment) to be investigated is loaded on an agarose gel. A constant voltage will then be applied and the negatively charged DNA-fragments will migrate toward the cathode. The larger the form of the fragment, the slower the migration along the gel. DNA of type I (most compact) moves fastest, type II slowest. The gel will then be put in solution which contains very little ethidium bromide. The DNA fragments are made visible by intercalation and irradiation with UV-light of 300 nm depicting red-orange colored fluorescence (590 nm). This method is so sensitive that less than 5 ng DNA per band are detected. In the photographic record of the gels in FIG. 5, the migration direction is from the top to the bottom.

1.2 Production of the Plasmids

Figure 5:
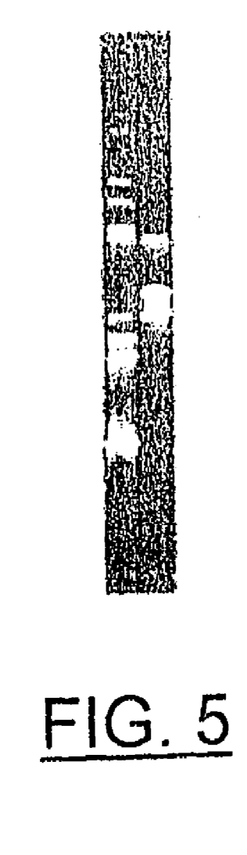
FIG. 5: ethidium bromide stained agarose gel of the three types I, II and III of DNA (left lane) and a molecular weight marker (right lane).

The plasmid Bluescript KS™ with a size of 2958 base pairs has been produced following the standard protocol of the company QIAGEN. Usually, this plasmid exists in the superhelix form (type I). With the restriction enzyme KpnI the linearized form of the plasmid DNA (type III) can be produced. A single strandbreak resulting in the relaxed circular form of plasmid (type II), can be induced by the enzyme DNAase I. FIG. 5, right lane, shows the electrophoresis on agarose-gel of a mixture of these three types of DNA. For the electrophoresis a marker with several sizes of DNA-pieces has been used as reference (left lane).

As demonstrated by the three bands of the right lane, the three types of DNA were clearly separated and can be distinguished after visualization. If single or double strand breaks result from conversion electrons, it should be easy detectable by this method.

Figure 6:
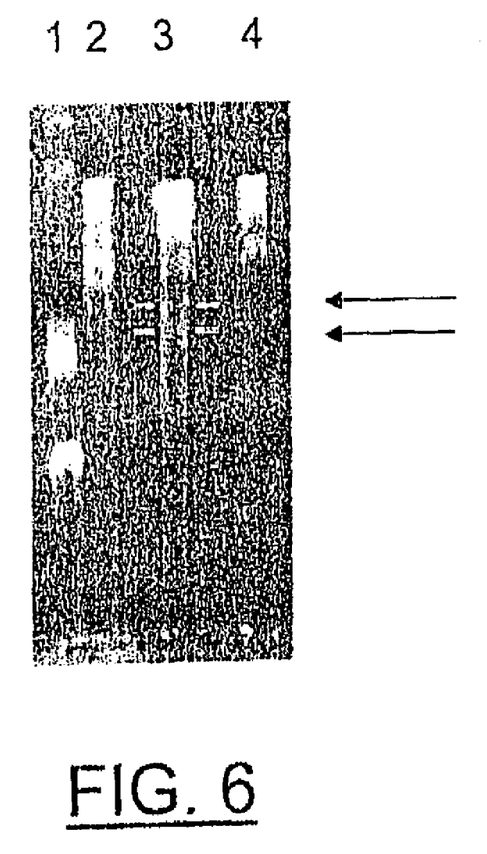
FIG. 6: ethidium bromide stained agarose gel of a plasmid preparation treated with the compound [$^{99m}Tc(P_1)$(teta)$(CO)_3$]; The application site of the sample is on the bottom of the gel. Lane 1 is the molecular weight marker; lane 2 is a reference solution containing supercoiled, relaxed (single strand break) and linearized (double strand break) plasmid, lane 3 is the experimental solution containing both plasmid and the intercalator of the invention, and lane 4 is the negative reference containing only plasmid.

2. Investigation of the Ability of $[^{99m}Tc(P_1)(teta)(CO)_3]$ to Induce Strandbreaks 5 μl of a solution containing approx. 0.3 mCi/ml of $[^{99m}Tc(P_1)(teta)(CO)_3]$ and 100 ng of type I plasmid (~=$3*10^{-5}$ M in base pairs) were left standing over a period of 18 hours. Then a electrophoresis of this mixture and the three references was made (FIG. 6).

It is clearly visible that the plasmids in the measurement solution (lane 3) migrate slower than in the reference solution. The reason for this observation is that a small change in the structure of the plasmids is probably induced by intercalation of the complex into the double strand. This change in the tertiary structure of the plasmid did then allow a better intercalation of the ethidium bromide, thus explaining the stronger intensity of the band of sample solution.

Furthermore, in the comparison with the negative reference solution (lane 4), it is obvious that one or possibly two new bands appeared (arrows) in the lane of the solution treated with the $^{99m}$Tc complex. The stronger of these two bands corresponds approximately to the position of type II on the band of reference solution in lane 2, containing the three types. This means that the complex has induced a single strand break in the plasmid.

The invention claimed is:

1. A compound comprising:
   a moiety having an affinity for cancer cells;
   an intercalating moiety coupled to the moiety having an affinity for cancer cells, wherein the intercalating moiety comprises at least one unsubstituted aromatic ring that shares two carbons with only one other aromatic ring, and is configured to insert into the structure of deoxyribonucleic acid, and wherein the intercalating moiety is functionalized with a ligand configured to coordinate a [metal(CO)$_3$]$^+$ moiety; and
   a metal complexed with the ligand attached to the intercalating moiety.

2. The compound of claim 1, wherein the metal is a radioactive metal.

3. The compound of claim 2 wherein the radioactive metal is a γ-emitting nuclide.

4. The compound of claim 2, wherein the radioactive metal comprises Tc-99m, Re-186, Re-188, or Mn, or combinations thereof.

5. The compound of claim 1, wherein the moiety having an affinity for cancer cells comprises a peptide, a protein, or any combination thereof.

6. The compound of claim 2, wherein the moiety having an affinity for cancer cells comprises a peptide, a protein, or any combination thereof.

7. The compound of claim 1, wherein the moiety having an affinity for cancer cells comprises a somatostatin-receptor binding molecule, a neurotensin-receptor binding molecule, a bombesin-receptor binding molecule, a GPIIb/IIIa-receptor binding molecule, an antibody, a penetratine, or a glycoprotein, or any combination thereof.

8. The compound of claim 2, wherein the moiety having an affinity for cancer cells comprises a somatostatin-receptor binding molecule, a neurotensin-receptor binding molecule, a bombesin-receptor binding molecule, a GPIIb/IIIa-receptor binding molecule, an antibody, a penetratine, or a glycoprotein, or any combination thereof.

9. The compound of claim 1, wherein the moiety having an affinity for cancer cells comprises an anti-sense oligonucleotide, a deoxy-uridine, or a spermidine, or any combination thereof.

10. The compound of claim 2, wherein the moiety having an affinity for cancer cells comprises an anti-sense oligonucleotide, a deoxy-uridine, or a spermidine, or any combination thereof.

11. A composition comprising:
    an excipient; and
    a compound comprising:
    a moiety having an affinity for cancer cells;
    an intercalating moiety coupled to the moiety having an affinity for cancer cells, wherein the intercalating moiety comprises at least one unsubstituted aromatic ring that shares two carbons with only one other aromatic ring, and is configured to insert into the structure of deoxyribonucleic acid, and wherein the intercalating moiety is functionalized with a ligand configured to coordinate a [metal(CO)$_3$]$^+$ moiety; and
    a metal complexed with the ligand attached to the intercalating moiety, wherein the metal comprises Tc-99m, Re-186, Re-188, or Mn, or combinations thereof.

12. The composition of claim 11, wherein the metal is a radioactive metal.

13. The composition of claim 11, wherein the moiety having an affinity for cancer cells comprises a peptide, a protein, or any combination thereof.

14. The composition of claim 12, wherein the moiety having an affinity for cancer cells comprises a peptide, a protein, or any combination thereof.

15. The composition of claim 11, wherein the moiety having an affinity for cancer cells comprises a somatostatin-receptor binding molecule, a neurotensin-receptor binding molecule, a bombesin-receptor binding molecule, a GPIIb/IIIa-receptor binding molecule, an antibody, a penetratine, or a glycoprotein, or any combination thereof.

16. The composition of claim 12, wherein the moiety having an affinity for cancer cells comprises a somatostatin-receptor binding molecule, a neurotensin-receptor binding molecule, a bombesin-receptor binding molecule, a GPIIb/IIIa-receptor binding molecule, an antibody, penetratine, or a glycoprotein, or any combination thereof.

17. The composition of claim 11, wherein the moiety having an affinity for cancer cells comprises an anti-sense oligonucleotide, a deoxy-uridine, or a spermidine, or any combination thereof.

18. The composition of claim 12, wherein the moiety having an affinity for cancer cells comprises an anti-sense oligonucleotide, a deoxy-uridine, or a spermidine, or any combination thereof.

19. A method of using a composition, the method comprising:
    administering a composition to a medical patient, wherein the composition includes a compound comprising:
    a moiety having an affinity for cancer cells;
    an intercalating moiety coupled to the moiety having an affinity for cancer cells, wherein the intercalating moiety comprises at least one unsubstituted aromatic ring that shares two carbons with only one other aromatic ring, and inserts into the structure of deoxyribonucleic acid, and wherein the intercalating moiety is functionalized with a ligand configured to coordinate a [metal(CO)$_3$]$^+$ moiety; and
    a metal complexed with the ligand attached to the intercalating moiety, wherein the ligand and the intercalating moiety provide at least a bidentate coupling to the metal.

20. The method of claim 19, wherein the composition is administered to diagnose at least one of a tumor or a malignancy.

21. The method of claim 19, wherein the composition is administered to treat at least one of a tumor or a malignancy.

22. The compound of claim 1, wherein the intercalating moiety comprises a planar, heterocyclic aromatic ring structure.

23. The compound of claim 1, wherein the intercalating moiety comprises acridine, ellipticine, carbazole, benzimidazole, or a compound that exhibits cytostatic activity, or any combination thereof.

24. The compound of claim 2, wherein the intercalating moiety comprises a planar, heterocyclic aromatic ring structure.

25. The compound of claim 2, wherein the intercalating moiety comprises acridine, ellipticine, phenanthroline, carbazole, benzimidazole, or a compound that exhibits cytostatic activity, or any combination thereof.

26. The compound of claim 11, wherein the intercalating moiety comprises a planar, heterocyclic aromatic ring structure.

27. The composition of claim 11, wherein the intercalating moiety comprises acridine, ellipticine, phenanthroline, carbazole, benzimidazole, or a compound that exhibits cytostatic activity, or any combination thereof.

28. The compound of claim 12, wherein the intercalating moiety comprises a planar, heterocyclic aromatic ring structure.

29. The composition of claim 12, wherein the intercalating moiety comprises acridine, ellipticine, phenanthroline, carbazole, benzimidazole, or a compound that exhibits cytostatic activity, or any combination thereof.

30. A compound comprising:
    a tumor seeking molecule, wherein the tumor seeking molecule has an affinity for a cancer cell, a tumor, or both;
    an intercalating moiety comprising a planar, heterocyclic aromatic ring structure coupled to the tumor seeking molecule, wherein the planar heterocyclic aromatic ring structure comprises at least one unsubstituted aromatic ring fused to only one other aromatic ring by two carbons, and wherein the intercalating moiety is functionalized with a ligand configured to coordinate a [metal $(CO)_3$]$^+$ moiety; and
    a metal complexed with the ligand attached to the intercalating moiety.

31. The compound of claim 30, wherein the tumor seeking molecule has an affinity for the cancer cell.

32. The compound of claim 30, wherein the tumor seeking molecule has an affinity for the tumor.

33. The compound of claim 30, comprising a structure of:

wherein the intercalating moiety is bound to the compound by two carbon bonds, wherein the intercalating moiety is bound to the compound by two carbon bonds, wherein the intercalating moiety is bound to the compound by two carbon bonds, or wherein M is the metal.

* * * * *